US011890167B2

(12) United States Patent
Olson

(10) Patent No.: US 11,890,167 B2
(45) Date of Patent: Feb. 6, 2024

(54) EAR CLEANER

(71) Applicant: Quest Products, LLC, Pleasant Prairie, WI (US)

(72) Inventor: Richard Carl Olson, Deerfield Beach, FL (US)

(73) Assignee: Quest Products, LLC, Pleasant Prairie, WI (US)

( * ) Notice: Subject to any disclaimer, the term of this patent is extended or adjusted under 35 U.S.C. 154(b) by 852 days.

(21) Appl. No.: 16/739,859

(22) Filed: Jan. 10, 2020

(65) Prior Publication Data

US 2020/0214895 A1 Jul. 9, 2020

Related U.S. Application Data

(63) Continuation of application No. 15/655,332, filed on Jul. 20, 2017, now Pat. No. 10,531,986, which is a continuation-in-part of application No. 29/567,975, filed on Jun. 14, 2016, now Pat. No. Des. 847,993.

(51) Int. Cl.
*A61F 11/00* (2022.01)

(52) U.S. Cl.
CPC ....... *A61F 11/006* (2013.01); *A61F 2240/001* (2013.01); *A61F 2250/0014* (2013.01); *A61F 2250/0037* (2013.01)

(58) Field of Classification Search
CPC .............................. A61F 11/00; A61F 11/006; A61F 2250/0014; A61F 2250/0037; A61B 17/22; A61B 17/50
See application file for complete search history.

(56) References Cited

U.S. PATENT DOCUMENTS

| 147,660 | A | 2/1874 | Leiner |
| 651,395 | A | 6/1900 | Stapp |
| D144,599 | S | 4/1946 | Tupper |
| 3,099,263 | A | 7/1963 | Palazzolo |
| 3,203,418 | A | 8/1965 | Johnston |
| 4,091,497 | A | 5/1978 | Bade |
| 4,411,265 | A | 10/1983 | Eichenlaub |
| 4,568,326 | A | 2/1986 | Rangaswamy |
| D296,005 | S | 5/1988 | Alkire |
| 4,746,238 | A | 5/1988 | Levine |
| 4,935,001 | A | 6/1990 | George |
| 5,107,861 | A | 4/1992 | Narboni |
| D327,322 | S | 6/1992 | Brewer, Jr. |
| 5,223,259 | A | 6/1993 | Lackney |
| D339,036 | S | 9/1993 | McDaniel |
| 5,334,212 | A | 8/1994 | Karell |

(Continued)

FOREIGN PATENT DOCUMENTS

| AU | 2013100584 | 8/2013 |
| EP | 0158543 | 10/1985 |

(Continued)

OTHER PUBLICATIONS

U.S. Appl. No. 29/684,273, filed Mar. 2019, Olson.

(Continued)

*Primary Examiner* — Vi X Nguyen
(74) *Attorney, Agent, or Firm* — Fitch, Even, Tabin & Flannery LLP

(57) ABSTRACT

An ear cleaner is provided that includes an elongated handle, a spoon, and a disc intermediate the spoon and the disc.

16 Claims, 3 Drawing Sheets

(56) References Cited

U.S. PATENT DOCUMENTS

| | | |
|---|---|---|
| 5,374,276 A | 12/1994 | Lay |
| D362,067 S | 9/1995 | Chang |
| 5,509,921 A | 4/1996 | Karell |
| 5,632,756 A | 5/1997 | Kruglick |
| 5,715,850 A | 2/1998 | Markgraaf |
| 5,738,643 A | 4/1998 | Stredic, III |
| D405,175 S | 2/1999 | Stredic, III |
| 5,888,199 A * | 3/1999 | Karell .................. A61F 11/006 606/162 |
| 5,897,568 A | 4/1999 | Vanraes |
| D414,866 S | 10/1999 | Szabo |
| D415,275 S | 10/1999 | Huttner |
| D420,133 S | 2/2000 | Huttner |
| 6,033,417 A | 3/2000 | Tseng |
| D422,360 S | 4/2000 | Young |
| 6,080,126 A | 6/2000 | Zygmont |
| D432,239 S | 10/2000 | Shimizu |
| D441,141 S | 4/2001 | Shalita |
| D444,556 S | 7/2001 | Estrem |
| 6,270,510 B1 | 8/2001 | Westendorf |
| D469,871 S | 2/2003 | Sand |
| 6,695,802 B1 | 2/2004 | Thompson |
| D489,131 S | 4/2004 | Gojcaj |
| D489,133 S | 4/2004 | Shimizu |
| D490,523 S | 5/2004 | Samborski |
| 6,736,826 B2 | 5/2004 | Begun |
| 6,939,360 B2 | 9/2005 | Crespo |
| D515,213 S | 2/2006 | Huttner |
| 7,070,603 B2 | 7/2006 | Eicoff |
| 7,074,230 B2 | 7/2006 | Olson |
| D545,431 S | 6/2007 | Khademhosseini |
| D546,948 S | 7/2007 | Huttner |
| D547,869 S | 7/2007 | Eckman |
| D560,800 S * | 1/2008 | Curtis .......................... D24/119 |
| D560,806 S | 1/2008 | Eckman |
| D567,373 S | 4/2008 | Irby |
| D603,046 S | 10/2009 | Frey |
| 7,658,745 B2 | 2/2010 | Olson |
| D631,957 S | 2/2011 | Perez |
| D638,985 S | 5/2011 | Limongi |
| 7,951,106 B1 | 5/2011 | Perez |
| D654,165 S | 2/2012 | Yates |
| D701,600 S | 3/2014 | Kauffman |
| 9,232,853 B2 | 1/2016 | Olson |
| 9,233,027 B1 | 1/2016 | Jackson |
| 9,278,030 B2 | 3/2016 | Olson |
| D757,938 S | 5/2016 | Jackson |
| 10,219,951 B2 | 3/2019 | Olson |
| D847,993 S | 5/2019 | Olson |
| 10,479,842 B2 | 11/2019 | Haley |
| 10,531,986 B2 | 1/2020 | Olson |
| 11,045,357 B2 | 6/2021 | Olson |
| D952,849 S | 5/2022 | Olson |
| 2001/0001828 A1 | 5/2001 | Begun |
| 2003/0135228 A1 | 7/2003 | Crespo |
| 2003/0187469 A1 | 10/2003 | Olson |
| 2005/0096678 A1 | 5/2005 | Olson |
| 2008/0300527 A1 | 12/2008 | Bivins |
| 2009/0248029 A1 | 10/2009 | Paulos |
| 2010/0312198 A1 | 12/2010 | Guidi |
| 2011/0179887 A1 | 7/2011 | Cobian |
| 2012/0296355 A1 | 11/2012 | Burres |
| 2013/0331804 A1 | 12/2013 | Nino |
| 2014/0031846 A1 | 1/2014 | Edme |
| 2014/0276893 A1 | 9/2014 | Schaller |
| 2017/0087024 A1 | 3/2017 | Al-Bakkour |
| 2017/0354541 A1 | 12/2017 | Olson |
| 2019/0159936 A1 | 5/2019 | Olson |
| 2021/0346206 A1 | 11/2021 | Olson |

FOREIGN PATENT DOCUMENTS

| | | |
|---|---|---|
| EP | 0234061 | 9/1987 |
| EP | 0875221 | 11/1998 |
| WO | 1996037172 | 11/1996 |

OTHER PUBLICATIONS

"Pictures of an Ear Cleaning Device and Its Retail Packaging." The ear cleaning device being publicly available before Jun. 14, 2016, 3 pages.

"Pictures of Another Clinere® Brand Ear Cleaner." The ear cleaning device being publicly available for purchase more than one year before Jul. 15, 2013, 3 pages.

"Pictures of Clinere® Brand Ear Cleaner." The ear cleaning device being publicly available for purchase more than one year before Jul. 15, 2013, 3 pages.

"Pictures of Ear Cleaner—Earvana 1." The ear cleaner being publicly available before Mar. 2013, 2 pages.

"Pictures of Ear Cleaner—Earvana 2." The ear cleaner being publicly available before Mar. 2013, 2 pages.

"Pictures of Ear Cleaner—Earvana 3." The ear cleaner being publicly available before Mar. 2013, 2 pages.

"Pictures of Ear Cleaner—Earvana 4." The ear cleaner being publicly available before Mar. 2013, 2 pages.

"Pictures of Ear Scrubber Ear Cleaner." The ear cleaner being publicly available Nov. 2015, 1 page.

"Pictures of Ototek Loop Ear Cleaner." The ear cleaner being publicly available for sale before Jul. 15, 2012, 3 pages.

"Pictures of Walgreens Brand Ear Cleaner." The ear cleaning device being publicly available for purchase on or about Jun. 29, 2017, 3 pages.

Clinere Earwax Cleaning Kit https://www.amazon.com/Clinere-Earwax-Cleaning-Kit/dp/BO101K30PI/ref=sr_1_3_s_it?s=hpc&ie=UTF8&qid=1522946098&sr=1-3&keywords=clinere#customerReviews Jan. 7, 2017 (Year: 2017).

Ototek Loop Ear Wax Removal https://www.amazon.com/Ototek-Loop-Ear-Wax-Removal/dp/B008BXLINQ/ref=cm_cr_arp_d_product_top?ie=UTF8 Aug. 13, 2012 (Year: 2012).

United States Patent Office, Office Action dated May 29, 2019, from related U.S. Appl. No. 15/655,332, 17 pages.

YouTube video entitled "Smart Swab," posted Sep. 4, 2014, screen captures and video description, 5 pages. <https://youtu.be/XNSpdXUwNuM>.

Response to Office Action filed May 20, 2005, from U.S. Appl. No. 10/369,915, 4 pages.

Response to Office Action filed Office Action dated Jan. 5, 2006, from U.S. Appl. No. 10/369,915, 8 pages.

USPTO, Final Office Action dated Mar. 5, 2021, from U.S. Appl. No. 29/684,273.

"Ototek Loop Ear Wax Removal." <https://www.amazon.com/Ototek-Loop-Ear-Wax-Removal/product-reviews/B008BXLINQ/ref=cm_cr_getr_d_paging_btm_next_35?ie=UTF8&reviewerType=all_reviews&sortBy=recent&pageNumber=3 5>, Aug. 13, 2012, 3 pages.

\* cited by examiner

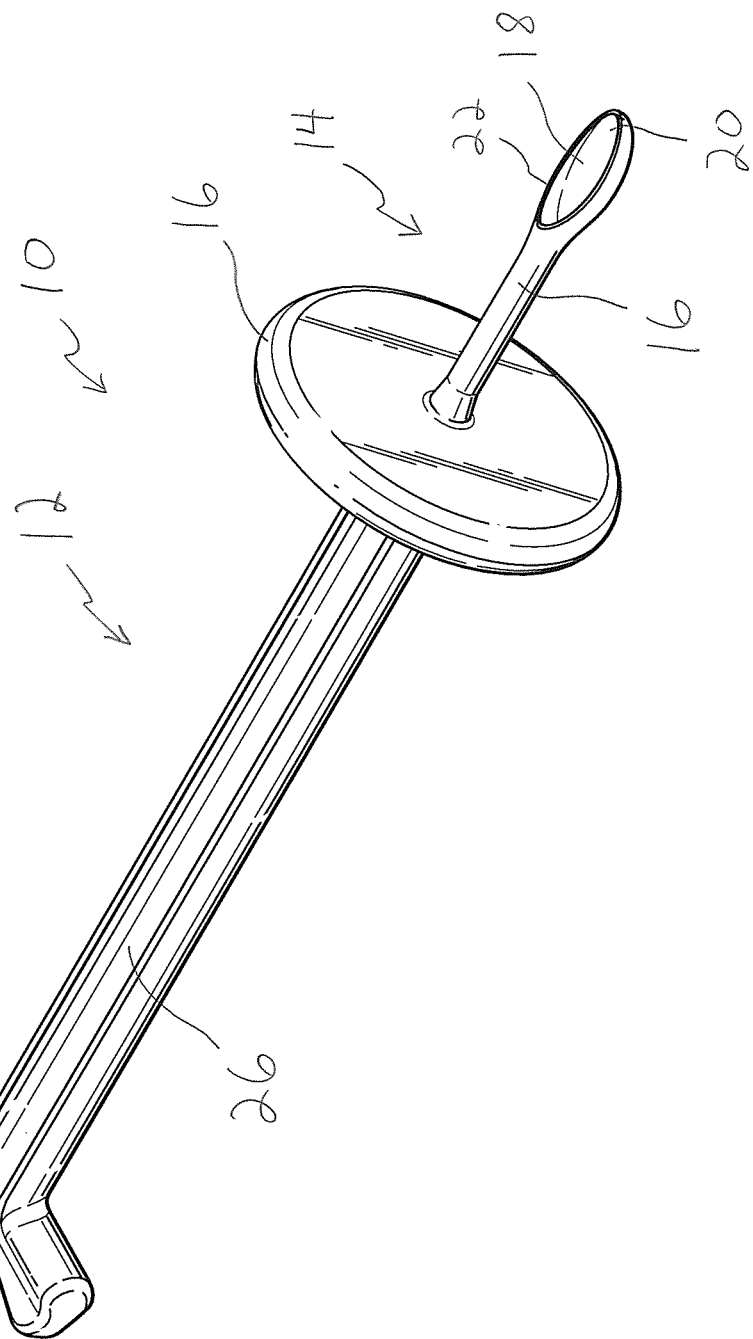

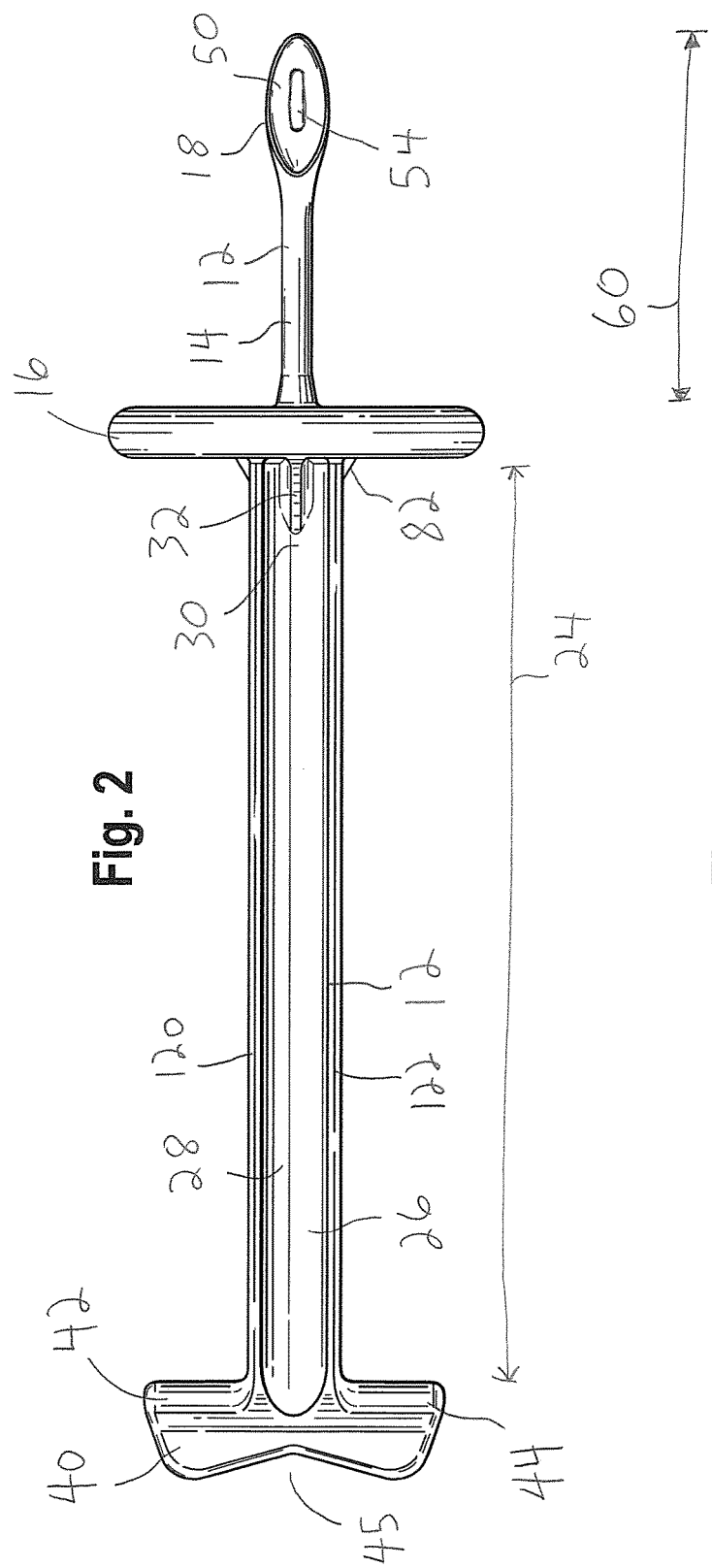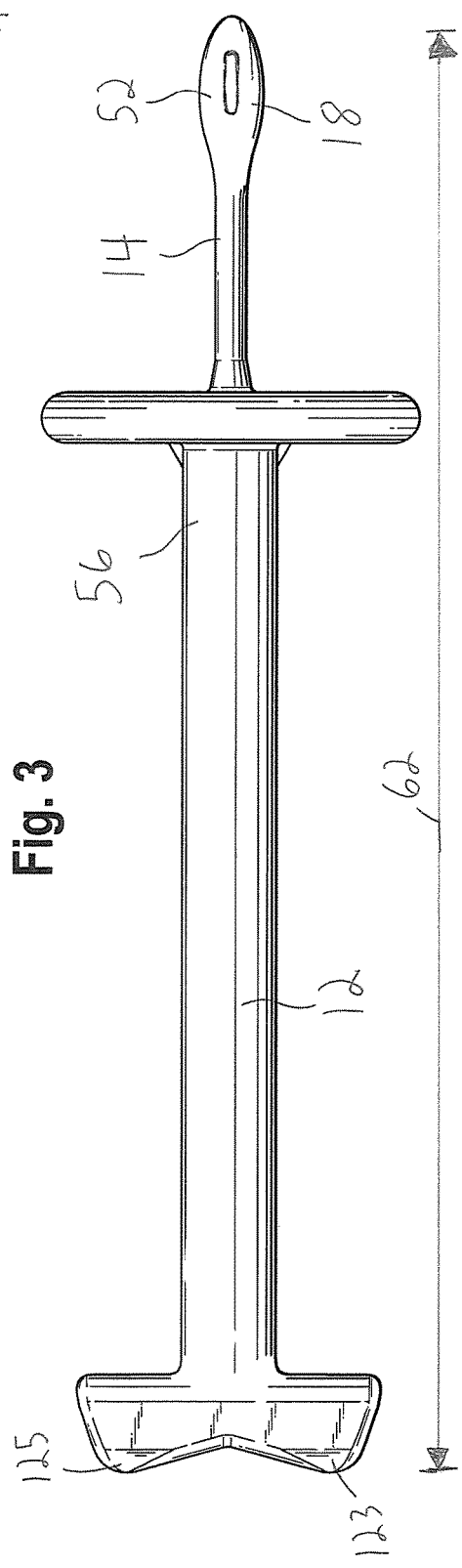

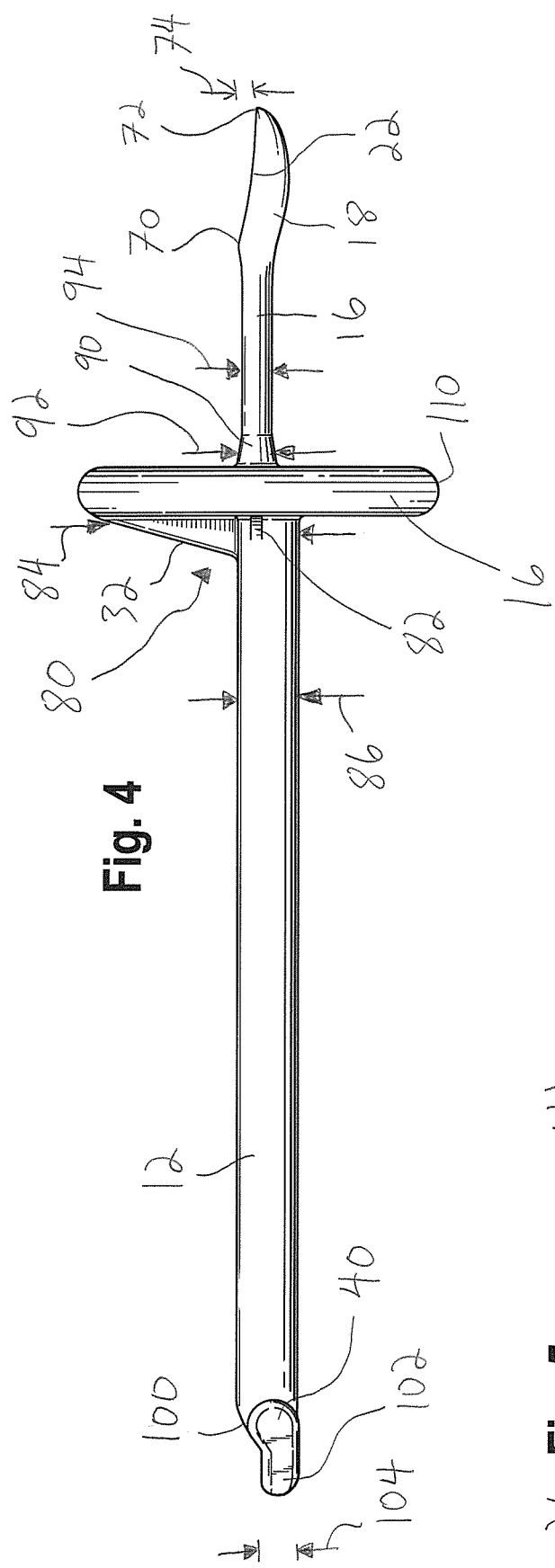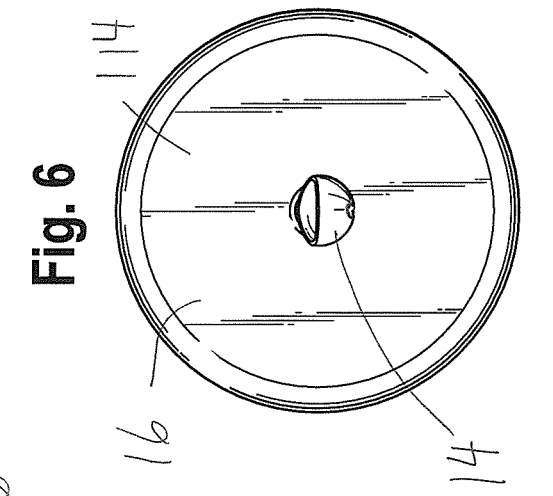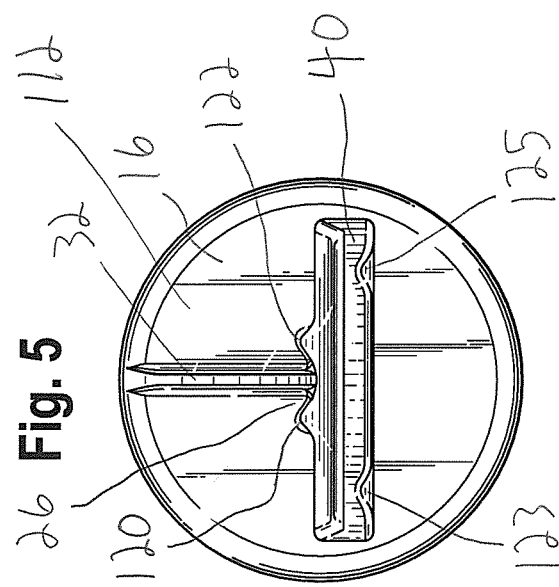

EAR CLEANER

CROSS-REFERENCE TO RELATED APPLICATIONS

This application is a continuation of U.S. patent application Ser. No. 15/655,332, filed on Jul. 20, 2017, which is a continuation-in-part of U.S. Design Patent Application No. 29/567,975, filed Jun. 14, 2016, now U.S. Design Patent No. D847,993, which are hereby incorporated by reference in their entireties.

FIELD

This disclosure relates to a device for ear cleaning.

BACKGROUND

Ear cleaners are known to remove debris, such as ear wax, from an ear.

BRIEF DESCRIPTION OF THE DRAWINGS

FIG. 1 is a perspective view of an ear cleaner;
FIG. 2 is a top plan view of the ear cleaner of FIG. 1;
FIG. 3 is a bottom plan view of the ear cleaner of FIG. 1;
FIG. 4 is a side elevational view of the ear cleaner of FIG. 1;
FIG. 5 is a rear elevational view of the ear cleaner of FIG. 1; and
FIG. 6 is a front elevational view of the ear cleaner of FIG. 1.

DETAILED DESCRIPTION

With reference to FIG. 1, an ear cleaner 10 is provided having a handle 12, a spoon 14, and a disc 16 intermediate the handle 12 and spoon 14. The spoon 14 includes a neck 16 and a bowl 18 for scooping debris off of a surface, such as removing ear wax from a user's ear. The bowl 18 includes an opening 20 and a rim 22 extending about the opening 20.

With reference to FIGS. 1 and 2, the handle 12 has a length 24 and a groove 26 extending along the handle 12 for a majority of the length 24, such as extending substantially the entire length 24. The groove 26 has an inwardly curved surface 28. The groove 26 facilitates manipulation of the ear cleaner 10 by permitting a user to advance a tip of her finger into the groove 26 to help steer the ear cleaner 10. The groove 26 includes a groove lower surface 30 and the ear cleaner 10 has material, such as a ramp 32, extending upwardly from the groove lower surface 30 toward the disc 16. The ramp 32 strengthens the ear cleaner 10.

The ear cleaner 10 also includes a transverse gripping portion 40 having portions 42, 44 that extend outward from the handle 12 transverse to the length 24 of the handle 12. The transverse gripping portion 40 has a recess 45, which may receive a user's finger.

With reference to FIGS. 2 and 3, the bowl 18 includes a bowl inner surface 50 and a bowl outer surface 52. The bowl 18 includes a slot 54 extending from the bowl inner surface 50 to the outer bowl surface 52. In one form, the slot 54 has a length oriented to extend parallel to the length 24 of the handle 12. The slot 54 may be elongated.

With reference to FIG. 3, the handle 12 includes an outwardly extending curved surface 56. The outwardly curved surface 56 may extend for a majority of the length 24 of the handle 12.

The spoon 14 has a length 60 that is less than the length 24 of the handle 12. Further, the ear cleaner 10 may have an overall length 62.

With reference to FIG. 4, the rim 22 of the bowl 18 has an upper rear edge 70 and an upper front edge 72. The upper front edge 72 is disposed a distance 74 below the upper rear edge 70.

The handle 12 includes a transition portion 80 that includes the ramp 32 and lateral ramps 82. The transition portion 80 includes a cross-sectional dimension 84 that is larger than a cross-sectional dimension 86 of the handle 12.

The neck 16 includes a tapered portion 90 having a cross-sectional dimension 92 that is larger than a cross-sectional dimension 94 of the neck 16.

With reference to FIG. 4, the traverse gripping portion 40 may have a tapered portion 100 that transitions to a thin portion 102. The thin portion 102 has a cross-sectional dimension 104 that is less than the dimension 86 of the handle 12.

With references to FIGS. 4-6, the disc 16 has a rounded annular edge 110 and flat surfaces 112, 114 on opposite sides of the disc 16.

With reference to FIG. 5, the groove of the handle 12 includes longitudinal edges 120, 122 on opposite sides of the groove 26. The longitudinal edges 120, 122 extend from the transverse gripping portion 40 to the disc 16. The longitudinal edges 120, 122 provide easy to grip structures extending along the handle 12. The outwardly curved surface 56 may extend from one of the longitudinal edges 120, 122, such as from one of the longitudinal edges 120, 122 to the other. The outwardly curved surface 56 may extend from one of the longitudinal edges 120, 122 around the handle 12.

The transverse gripping portion 40 includes undercuts 123, 125 that form recesses in the transverse gripping portion 40.

The ear cleaner may have a unitary, one-piece construction. The ear cleaner may be made of plastic, such as injection-molded plastic.

While the foregoing description is with respect to specific examples, those skilled in the art will appreciate that there are numerous variations of the above that fall within the scope of the concepts described herein and the appended claims.

What is claimed is:

1. An ear cleaner having a longitudinal axis, the ear cleaner comprising:
   an elongate handle;
   a spoon having an interior and a leading end;
   a disc is intermediate the handle and the spoon;
   an upper opening of the spoon that opens to the interior of the spoon;
   an elliptical upper rim of the spoon extending about the upper opening;
   a bowl inner surface of the spoon extending downwardly into the spoon from the upper rim;
   a first arcuate upper edge of the upper rim;
   a second arcuate upper edge of the upper rim across the upper opening of the spoon from the first arcuate upper edge;
   an upper front edge of the upper rim of the spoon at the leading end thereof, the upper front edge connecting the first and second arcuate upper edges of the upper rim;
   an upper rear edge of the upper rim of the spoon across the upper opening of the spoon from the upper front edge, the upper rear edge connecting the first and second arcuate upper edges of the upper rim; and wherein the upper front edge of the upper rim of the spoon is lower than the upper rear edge and the upper opening of the spoon is inclined relative to the longitudinal axis of the ear cleaner.

2. The ear cleaner of claim 1 wherein the handle has a length and a finger-engaging groove that extends along the length of the handle.

3. The ear cleaner of claim 1 wherein the handle includes a length, a pair of longitudinal edges extending along the length, and a surface extending transverse to the length from one longitudinal edge to the other longitudinal edge; and
    a ramp surface extending upwardly from the surface toward the disc.

4. The ear cleaner of claim 1 wherein the handle has a length and a pair of longitudinal edges extending along the length of the handle.

5. The ear cleaner of claim 4 wherein the longitudinal edges each include a first portion that extends parallel to the first portion of the other longitudinal edge and a second portion that extends toward the second portion of the other longitudinal edge.

6. The ear cleaner of claim 4 wherein the longitudinal edges extend for at least a majority of the length of the handle.

7. The ear cleaner of claim 1 wherein the ear cleaner has a unitary, one-piece construction.

8. The ear cleaner of claim 1 wherein the spoon includes a slot and the bowl inner surface extends downward from the upper rim of the spoon to the slot.

9. The ear cleaner of claim 1 further comprising a neck connecting the spoon to the disc.

10. An ear cleaner comprising:
an elongate handle;
a spoon having a leading end;
a disc intermediate the handle and the spoon;
an upper rim of the spoon;
a bowl inner surface of the spoon extending downwardly into the spoon from the upper rim;
an upper front edge of the upper rim of the spoon at the leading end thereof;
an upper rear edge of the upper rim of the spoon across the spoon from the upper front edge;
wherein the upper front edge of the upper rim of the spoon is lower than the upper rear edge;
wherein the handle has a length and a pair of longitudinal edges extending along the length of the handle; and
wherein the longitudinal edges are separated by a groove extending longitudinally along the length of the handle.

11. An ear cleaner comprising:
an elongate handle;
a spoon having a leading end;
a disc intermediate the handle and the spoon;
an upper rim of the spoon;
a bowl inner surface of the spoon extending downwardly into the spoon from the upper rim;
an upper front edge of the upper rim of the spoon at the leading end thereof;
an upper rear edge of the upper rim of the spoon across the spoon from the upper front edge;
wherein the upper front edge of the upper rim of the spoon is lower than the upper rear edge;
wherein the handle has a length; and
a transverse gripping portion including portions extending outward from the handle transverse to the length of the handle.

12. The ear cleaner of claim 11 wherein the transverse gripping portion includes a recess to receive a user's finger.

13. The ear cleaner of claim 11 wherein the handle has a length and a finger-engaging groove that extends along the length of the handle.

14. The ear cleaner of claim 11 wherein the ear cleaner has a unitary, one-piece construction.

15. The ear cleaner of claim 11 wherein the spoon includes a slot and the bowl inner surface extends downward from the upper rim of the spoon to the slot.

16. The ear cleaner of claim 11 further comprising a neck connecting the spoon to the disc.

\* \* \* \* \*